United States Patent
O'Brien, III

(10) Patent No.: US 9,636,491 B1
(45) Date of Patent: May 2, 2017

(54) DISPOSABLE NEEDLE CARTRIDGES HAVING ABSORBING CONTAMINANT BARRIERS

(71) Applicant: Thomas Michael O'Brien, III, Dallas, TX (US)

(72) Inventor: Thomas Michael O'Brien, III, Dallas, TX (US)

(73) Assignee: Eclipse Aesthetics, LLC, Dallas, TX (US)

( * ) Notice: Subject to any disclaimer, the term of this patent is extended or adjusted under 35 U.S.C. 154(b) by 0 days.

(21) Appl. No.: 15/176,223

(22) Filed: Jun. 8, 2016

(51) Int. Cl.
*A61M 5/00* (2006.01)
*A61M 37/00* (2006.01)
*A61M 5/32* (2006.01)
*A61M 5/31* (2006.01)

(52) U.S. Cl.
CPC ...... *A61M 37/0015* (2013.01); *A61M 5/3297* (2013.01); *A61M 2005/3117* (2013.01); *A61M 2037/0023* (2013.01)

(58) Field of Classification Search
CPC ............ A61M 37/0015; A61M 5/3297; A61M 2037/0023; A61M 2005/3117
USPC .................................. 604/173, 117
See application file for complete search history.

(56) References Cited

U.S. PATENT DOCUMENTS

| | | | |
|---|---|---|---|
| 2,578,812 A | * | 12/1951 | Kollsman ............... A61M 5/28 604/117 |
| 2,588,623 A | | 3/1952 | Eliscu et al. |
| 2,840,076 A | | 6/1958 | Robbins |
| 4,159,659 A | | 7/1979 | Nightingale |
| 4,204,438 A | | 5/1980 | Binaris et al. |
| 4,582,060 A | | 4/1986 | Bailey |

(Continued)

FOREIGN PATENT DOCUMENTS

| | | |
|---|---|---|
| CA | 2340248 A1 | 2/2000 |
| CA | 2696209 A1 | 2/2009 |

(Continued)

OTHER PUBLICATIONS

Dermapen, Retrieved on Aug. 29, 2016 from http://dermapen.com/dermapen/, 2 pages.

(Continued)

*Primary Examiner* — Edelmira Bosques
(74) *Attorney, Agent, or Firm* — Vincent J. Allen; James H. Ortega; Carstens & Cahoon, LLP

(57) ABSTRACT

Disclosed herein are unique needle cartridges for use with transdermal microneedling devices, and prevent backflow of liquid(s) from the skin of a patient. One embodiment may comprise a base portion and a sleeve coupled to the base portion. The needle cartridge may also comprise a needle unit disposed at the distal end of the base portion and within the sleeve, wherein the needle unit comprises at least one needle ending therefrom. Also, the needle cartridge comprises a drive shaft disposed through the base portion and coupled to the needle unit, and configured to be driven reciprocally along a longitudinal axis of the base portion and thereby move the needle unit reciprocally such that the needles of the needle unit extend beyond and retract within the sleeve. Such needle cartridges would include an absorbing barrier disposed within the base portion to prevent the backflow of liquid(s) from the needle unit by absorbing such liquid(s).

51 Claims, 8 Drawing Sheets

(56) References Cited

U.S. PATENT DOCUMENTS

| | | |
|---|---|---|
| 4,671,277 A | 6/1987 | Beuchat |
| 4,782,725 A | 11/1988 | Spaulding |
| 4,796,624 A | 1/1989 | Trott et al. |
| 4,798,582 A | 1/1989 | Sarath et al. |
| 5,279,552 A | 1/1994 | Magnet |
| 5,514,150 A | 5/1996 | Rostoker |
| 5,551,319 A | 9/1996 | Spaulding et al. |
| 5,676,684 A | 10/1997 | Choi |
| 5,697,901 A | 12/1997 | Eriksson |
| 5,735,868 A | 4/1998 | Lee |
| 5,741,290 A | 4/1998 | Hsieh |
| 5,935,096 A | 8/1999 | Barrett |
| 5,976,167 A | 11/1999 | Lee |
| 6,080,172 A | 6/2000 | Fujiwara et al. |
| 6,332,871 B1 | 12/2001 | Douglas et al. |
| 6,345,553 B1 | 2/2002 | Adler et al. |
| 6,503,231 B1 | 1/2003 | Prausnitz et al. |
| 6,505,530 B2 | 1/2003 | Adler et al. |
| 6,793,633 B2 | 9/2004 | Douglas et al. |
| 6,890,319 B1 | 5/2005 | Crocker |
| 7,207,242 B1 | 4/2007 | Daigle |
| 7,340,980 B2 | 3/2008 | Conti Vecchi |
| 7,422,574 B2 | 9/2008 | Eriksson et al. |
| 7,470,237 B2 | 12/2008 | Beckman et al. |
| 7,618,429 B2 | 11/2009 | Mulholland |
| 7,695,486 B2 | 4/2010 | Dixon |
| 7,908,943 B2 | 3/2011 | Beyer |
| 8,029,527 B2 | 10/2011 | Lisec |
| 8,202,249 B2 | 6/2012 | Iio et al. |
| 8,236,021 B2 | 8/2012 | Kluge et al. |
| 8,454,643 B2 | 6/2013 | Crockett |
| 8,556,828 B2 | 10/2013 | Amano et al. |
| 8,666,487 B2 | 3/2014 | Kang |
| 8,794,109 B2 | 8/2014 | Lee |
| 8,900,194 B2 | 12/2014 | Clarke et al. |
| 8,920,379 B2 | 12/2014 | Lee |
| 8,945,056 B2 | 2/2015 | Iio et al. |
| 9,005,158 B2 | 4/2015 | Danenberg et al. |
| 9,044,582 B2 | 6/2015 | Chang et al. |
| 2003/0195542 A1 | 10/2003 | Lee |
| 2005/0010236 A1 | 1/2005 | Frister |
| 2005/0137525 A1 | 6/2005 | Wang et al. |
| 2005/0222565 A1 | 10/2005 | Manstein |
| 2005/0283125 A1 | 12/2005 | Barkhahn et al. |
| 2006/0047254 A1 | 3/2006 | Akahoshi |
| 2007/0038181 A1* | 2/2007 | Melamud ........... A61B 17/3478 604/158 |
| 2008/0009802 A1 | 1/2008 | Lambino et al. |
| 2008/0009811 A1 | 1/2008 | Cantor |
| 2008/0027384 A1 | 1/2008 | Wang et al. |
| 2008/0119781 A1 | 5/2008 | King |
| 2008/0214987 A1 | 9/2008 | Xu |
| 2008/0306502 A1 | 12/2008 | Lisec et al. |
| 2009/0125050 A1 | 5/2009 | Dixon |
| 2009/0137945 A1 | 5/2009 | Marquez |
| 2009/0209992 A1 | 8/2009 | McConchie |
| 2009/0222000 A1 | 9/2009 | Pacey |
| 2009/0318833 A1 | 12/2009 | Lim |
| 2009/0326571 A1 | 12/2009 | Mulholland |
| 2010/0023003 A1 | 1/2010 | Mulholland |
| 2010/0030152 A1 | 2/2010 | Lee et al. |
| 2010/0049126 A1 | 2/2010 | Bronfeld et al. |
| 2010/0286618 A1 | 11/2010 | Choi |
| 2011/0125179 A1 | 5/2011 | Dell'Aquila et al. |
| 2011/0230839 A1 | 9/2011 | Bahrami et al. |
| 2012/0123462 A1 | 5/2012 | Lee |
| 2012/0158032 A1 | 6/2012 | Jarling |
| 2012/0158100 A1 | 6/2012 | Schomacker |
| 2012/0271335 A1 | 10/2012 | Lee |
| 2012/0296280 A1 | 11/2012 | Eum |
| 2014/0018835 A1 | 1/2014 | Scherkowski et al. |
| 2014/0066864 A1 | 3/2014 | Eum |
| 2014/0094742 A1 | 4/2014 | Won |
| 2014/0094837 A1 | 4/2014 | Danenberg |
| 2014/0343481 A1 | 11/2014 | Ignon |
| 2015/0025561 A1 | 1/2015 | La Fontaine |
| 2015/0057604 A1 | 2/2015 | Arami et al. |
| 2015/0133862 A1 | 5/2015 | Bang |
| 2015/0151098 A1 | 6/2015 | Spendlove et al. |
| 2015/0201825 A1 | 7/2015 | Na |
| 2015/0351798 A1 | 12/2015 | Bourland et al. |
| 2015/0352346 A1 | 12/2015 | Webb |
| 2015/0359559 A1 | 12/2015 | Scherkowski |
| 2016/0074646 A1 | 3/2016 | Norman |
| 2016/0121093 A1 | 5/2016 | Fan |
| 2016/0175573 A1 | 6/2016 | Groop et al. |

FOREIGN PATENT DOCUMENTS

| | | |
|---|---|---|
| CA | 2568482 C | 2/2011 |
| CA | 2688510 A1 | 4/2011 |
| CN | 1256930 C | 5/2006 |
| CN | 10053569 C | 10/2009 |
| CN | 101557848 A | 10/2009 |
| CN | 102271608 A | 12/2011 |
| CN | 202173684 U | 3/2012 |
| CN | 101605536 B | 5/2012 |
| CN | 202740626 U | 2/2013 |
| CN | 202961504 U | 6/2013 |
| CN | 204017141 U | 12/2014 |
| CN | 204411493 U | 6/2015 |
| CN | 103272326 B | 8/2015 |
| CN | 103282077 B | 8/2015 |
| DE | 4331442 A1 | 3/1995 |
| DE | 19836376 A1 | 2/2000 |
| DE | 202004010659 U1 | 10/2004 |
| DE | 19781097 B4 | 7/2006 |
| DE | 102008031907 A1 | 1/2010 |
| EP | 0955359 B1 | 11/1999 |
| EP | 1104315 B1 | 11/2004 |
| EP | 1495782 B1 | 1/2005 |
| EP | 1576982 B1 | 9/2005 |
| EP | 1679039 B1 | 7/2006 |
| EP | 1882491 B1 | 1/2008 |
| EP | 1958659 B1 | 8/2008 |
| EP | 1992387 A2 | 11/2008 |
| EP | 2178585 A2 | 4/2010 |
| EP | 2324877 A1 | 5/2011 |
| EP | 2450080 A2 | 5/2012 |
| EP | 2462979 B1 | 6/2012 |
| EP | 2633882 A1 | 9/2013 |
| EP | 2653061 B1 | 10/2013 |
| EP | 2420265 B1 | 11/2014 |
| EP | 2835147 A1 | 2/2015 |
| EP | 2944349 A1 | 11/2015 |
| EP | 2954925 A1 | 12/2015 |
| EP | 2954926 A1 | 12/2015 |
| GB | 1444355 | 7/1976 |
| GB | 2234420 A | 2/1991 |
| GB | 2514444 A | 11/2014 |
| GB | 2518021 A | 3/2015 |
| JP | 10127732 A2 | 5/1998 |
| JP | 2000177289 A | 6/2000 |
| JP | 3097600 B2 | 10/2000 |
| JP | 2001293095 A | 10/2001 |
| JP | 2010514479 T2 | 5/2010 |
| JP | 2011167476 A | 9/2011 |
| JP | 4983180 B2 | 7/2012 |
| JP | 5539396 B2 | 7/2014 |
| KR | 20100007720 U | 7/2010 |
| KR | 101395099 A | 1/2014 |
| KR | 101457437 A | 7/2014 |
| KR | 101494219 B1 | 2/2015 |
| WO | 8701337 | 3/1987 |
| WO | 9742888 | 11/1997 |
| WO | 0009184 | 2/2000 |
| WO | 2004009172 A1 | 1/2004 |
| WO | 2004075971 A1 | 9/2004 |
| WO | 2005000382 A3 | 1/2005 |
| WO | 2007015232 A1 | 2/2007 |
| WO | 2007091671 A1 | 8/2007 |
| WO | 2008147117 A2 | 4/2008 |
| WO | 2008080109 A1 | 7/2008 |
| WO | 2008081444 A2 | 7/2008 |

(56) References Cited

FOREIGN PATENT DOCUMENTS

| WO | 2009023798 A2 | 2/2009 |
|---|---|---|
| WO | 2009070657 A2 | 6/2009 |
| WO | 2009145447 A1 | 12/2009 |
| WO | 2010085059 A2 | 7/2010 |
| WO | 2011039728 A1 | 4/2011 |
| WO | 2011093674 A2 | 8/2011 |
| WO | 2012057425 A1 | 5/2012 |
| WO | 2012077943 A2 | 6/2012 |
| WO | 2012140643 A1 | 10/2012 |
| WO | 2013180422 A1 | 12/2013 |
| WO | 2014004644 A1 | 1/2014 |
| WO | 2014110016 A1 | 7/2014 |
| WO | 2014151104 A1 | 9/2014 |
| WO | 2015119376 A1 | 8/2015 |
| WO | 2015163731 A1 | 10/2015 |
| WO | 2015188174 A1 | 12/2015 |
| WO | 2016022865 A1 | 2/2016 |

OTHER PUBLICATIONS

BeautyPen, Retrived on Aug. 29, 2016 from http://www.ibeautymachine.com/motorized-micro-needle-system-12-needle-rechargeable.html, 20 pages.
Eclipse MicroPen, Retrieved on Aug. 29, 2016 from http://www.eclipsemicropen.com/about/eclipse-micropen/, 7 pages.
SkinPen Precision webpages, Bellus Medical, http://insidesales.skinpen.com, www.skinpen.com, 5 pgs.
Yan et al, Enhancing DNA Delivery into the Skin with a Motorized Microneedle, European Journal of Pharmaceutical Sciences 52 (2014) 215-222, 8 pgs.
Bomtech Electronics Co. Ltd. Motorized Micro Needle Therapy, http://bomtech.net/product/medical_8.htm, 1 pg.

\* cited by examiner

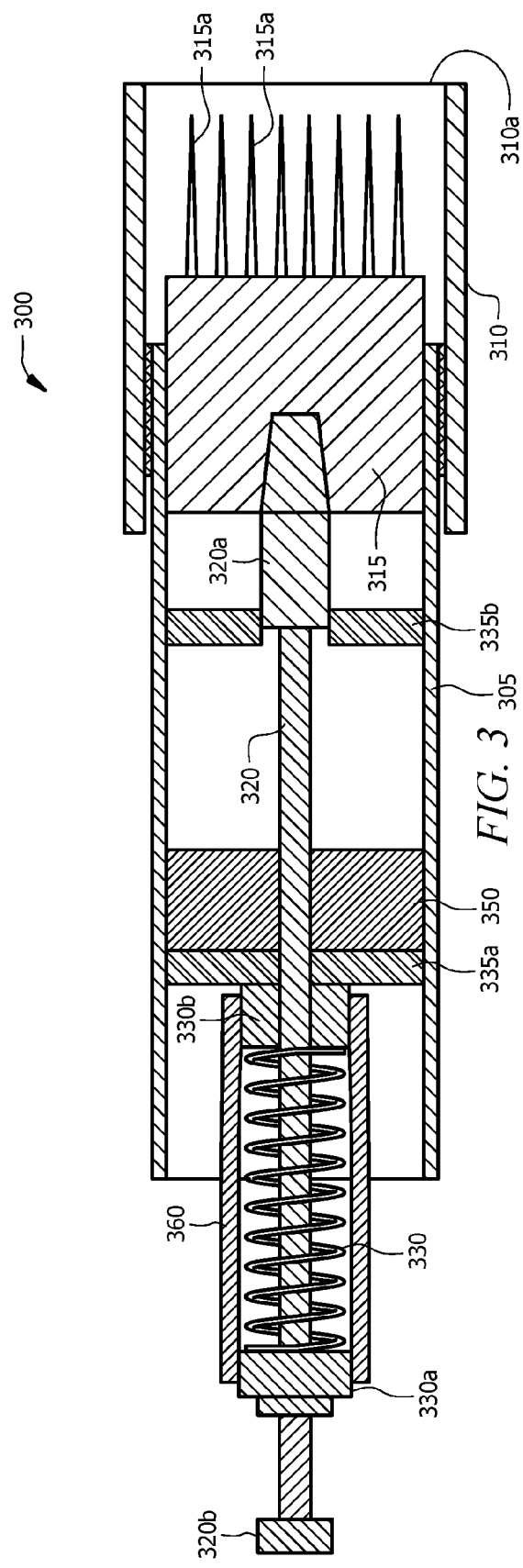
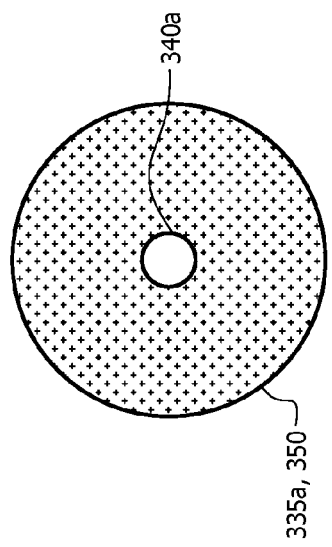
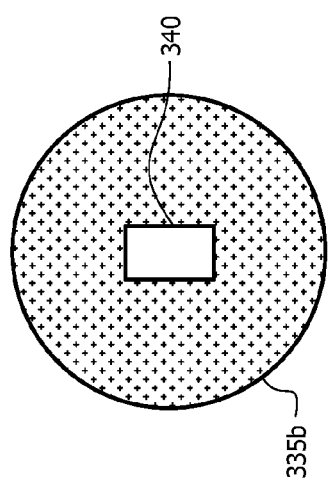
FIG. 3A
FIG. 3B
FIG. 3

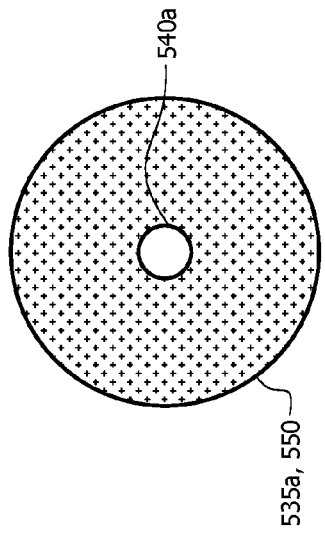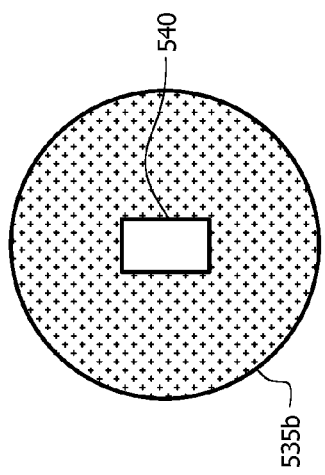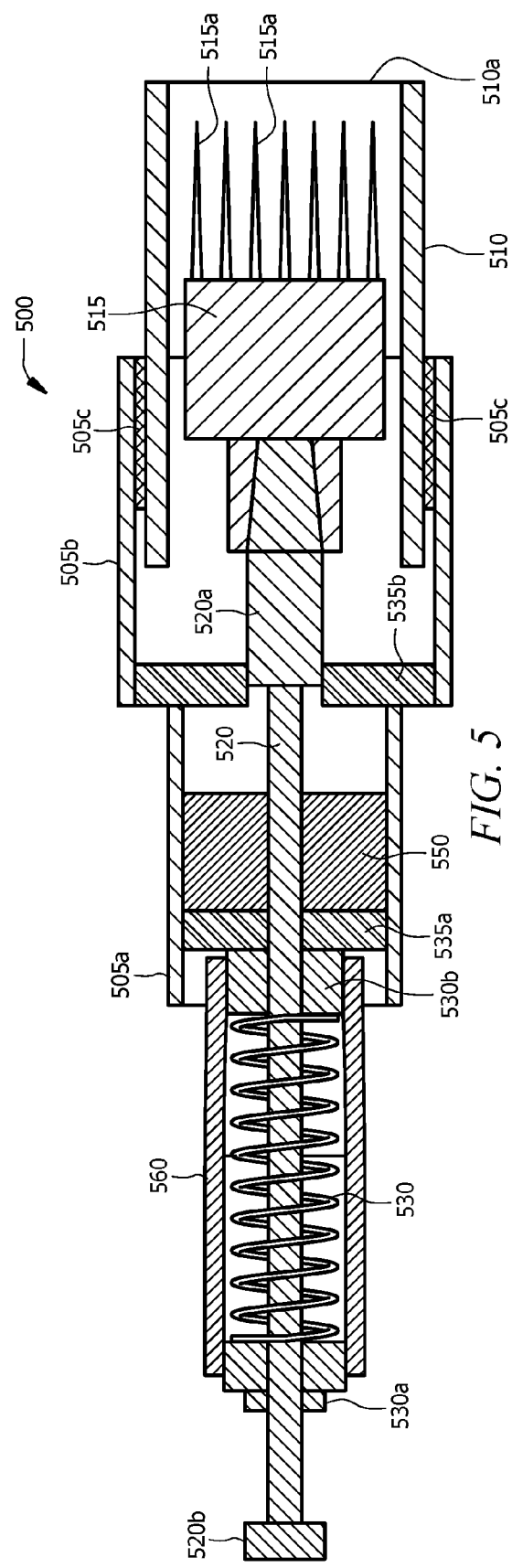

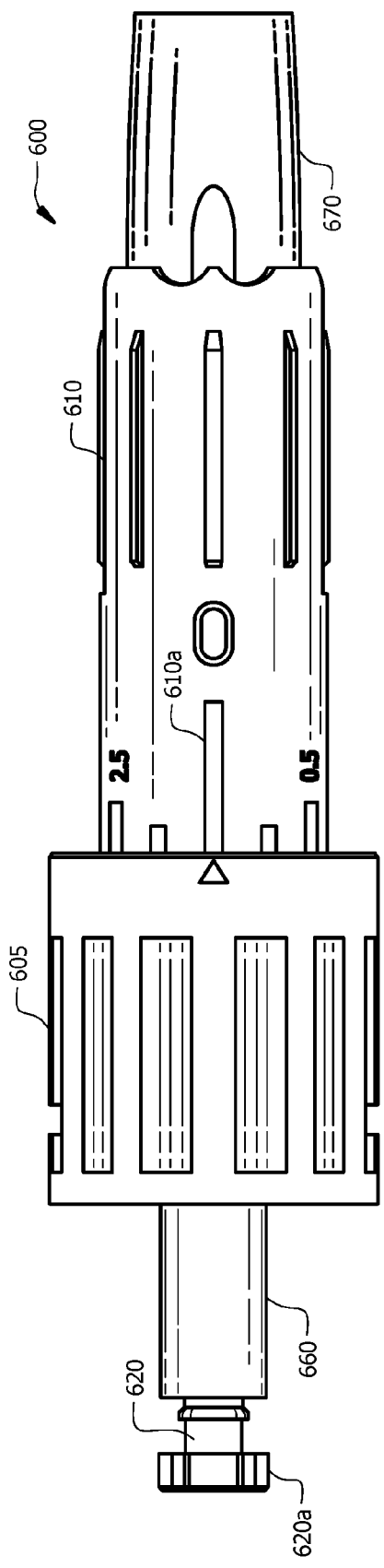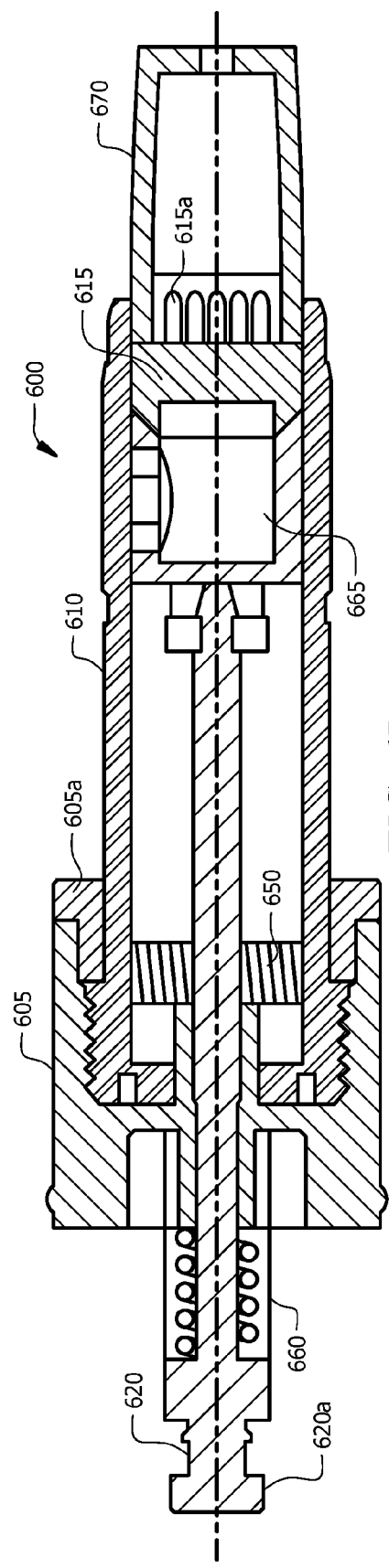

DISPOSABLE NEEDLE CARTRIDGES HAVING ABSORBING CONTAMINANT BARRIERS

TECHNICAL FIELD

The present disclosure relates to dermatological microneedling apparatuses, and in particular to disposable needle cartridges for use with dermatological microneedling apparatuses that provide an absorbing barrier that prevents liquid contaminants from flowing back through the cartridge and reaching the main body of the apparatus.

BACKGROUND

Typically, dermatological microneedling apparatuses indicate apparatuses that are used in an aesthetic transdermal procedure that involves repeatedly puncturing the skin with tiny, sterile needles (so-called "microneedling" the skin). In addition, many liquid injection apparatuses include those microneedling procedures performed for injecting a tattooing pigment or liquid/gel medicine, collagen or other items, into the skin or in an affected area of the skin for aesthetic purposes. Such microneedling apparatuses typically includes a needle cartridge having one or more needles therein, where the entire needle cartridge is disposable in order to prevent contamination from one patient to another. To accomplish this, such apparatuses provide for a detachable needle cartridge that include a needle unit and which mount to the front end of the microneedling apparatus during use.

However, although conventional microneedling apparatuses use disposable needle cartridges, blood and other liquids oozing out of the skin during use of the apparatus on a patient frequently flows into a (re-useable) main body of the microneedling apparatus along the disposable needle cartridge during a procedure. In early apparatuses, only a mechanical connection between a needle unit or cartridge and the main body existed, which could not block the small amount of the blood (or other liquids) flowing back into the apparatus body from the needle unit or cartridge, and therefore the blood or other contaminating liquids of the previously operated person remained in the main body after the liquid injection apparatus was used, even if the needle unit or cartridge were replaced before the next patient. This resulted in an unacceptable risk of contaminating the next patient with the blood or other liquids from the prior patient.

In newer conventional apparatuses, seals have been employed within the disposable needle cartridge in an attempt to either block contaminating fluids from flowing back into the main body of the device, or to capture such fluids flowing back through the needle cartridge. Such an exemplary attempt may be seen in U.S. Pat. No. 8,920,379 to Lee. Unfortunately, these needle cartridges rely on attempting to hermetically seal the components of the needle cartridge from the main body of the microneedling device or "pen." But even the implementation of seals that are intended to be airtight, the "sealed" cartridges still cannot thoroughly prevent contaminants flowing back into the main body of the apparatus. For example, with the Lee design in the '379 patent, the rubber material employed to provide seals between the needle unit and the reciprocating shaft that moves the needle unit in and out during use of the apparatus still allows the leaking of some fluids from the cartridge to the main body of the apparatus. Such leaking is caused by the quick movement of the components the sealing member is intended to hermetically grasp during use of the apparatus, and thus maintaining an airtight seal on such quickly moving components has proven to be troublesome, if not impossible. Accordingly, even with these new designs attempting to create airtight seals between the cartridge and the main body of the pen device, it has proven difficult for such conventional liquid injection devices to completely block liquid contaminants from flowing back into the main body of the apparatus, which then contaminate the new needle cartridge employed for the next person.

Accordingly, there is a need in the art for a disposable needle cartridge that can more effectively block liquid contaminants from flowing back through the cartridge and contaminating the main body of the apparatus, but which does not suffer from the deficiencies of the prior art mentioned above. The present disclosure provides such solutions.

SUMMARY

To overcome the deficiencies of the prior art, the disclosed principles provide for various embodiments of disposable needle cartridges for use with dermatological microneedling devices, including liquid injection devices, that provide an absorbing barrier that prevents liquid contaminants from flowing back through the cartridge and reaching the main body of the device. In one embodiment, such a needle cartridge may comprise a base portion having a proximal end located proximate to the microneedling device, and having a distal end opposite its proximal end. The needle cartridge may also comprise a sleeve having a proximal end coupled to the distal end of the base portion, and having a distal end opposite its proximal end. Furthermore, the needle cartridge may comprise a needle unit disposed at the distal end of the base portion and within the sleeve, wherein the needle unit comprises at least one needle ending therefrom towards the distal end of the sleeve. Also in such embodiments, the needle cartridge comprises a drive shaft disposed through the base portion and coupled to the needle unit, wherein the drive shaft is configured to be driven reciprocally along a longitudinal axis of the base portion by a drive system of the apparatus, and thereby move the needle unit reciprocally along the longitudinal axis of the base portion such that the needles of the needle unit extend beyond and retract within the distal end of the sleeve. Still further, such needle cartridges in accordance with the disclosed principles may also include an absorbing barrier disposed within the base portion and configured to prevent the backflow of liquid from the needle unit through the base portion during use of the apparatus. Numerous embodiments and advantages associated with each such embodiment are discussed in further detail below.

BRIEF DESCRIPTION OF THE DRAWINGS

The detailed description that follows, by way of non-limiting examples of embodiments, makes reference to the noted drawings in which reference numerals represent the same parts throughout the several views of the drawings, and in which:

FIG. 3 illustrates a cross-sectional side view of another embodiment of a disposable needle cartridge constructed in accordance with the disclosed principles;

FIG. 3A illustrates a top view of an exemplary shape for one of the support members in the embodiment of the disposable needle cartridge illustrated in FIG. 3;

FIG. 3B illustrates a top view of an exemplary shape for another of the support members and/or the absorbing member in the embodiment of the disposable needle cartridge illustrated in FIG. 3;

FIG. 5 illustrates a cross-sectional side view of yet another embodiment of a disposable needle cartridge constructed in accordance with the disclosed principles;

FIG. 5A illustrates a top view of an exemplary shape for one of the support members in the embodiment of the disposable needle cartridge illustrated in FIG. 5;

FIG. 5B illustrates a top view of an exemplary shape for another of the support members and/or the absorbing member in the embodiment of the disposable needle cartridge illustrated in FIG. 5;

FIG. 6A illustrates a side view of another embodiment of a disposable needle cartridge constructed in accordance with the disclosed principles;

FIG. 6B illustrates a cross-sectional side view of the embodiment of a disposable needle cartridge illustrated in FIG. 6A;

DETAILED DESCRIPTION

In view of the foregoing, through one or more various aspects, embodiments and/or specific features or sub-components, the present disclosure is thus intended to bring out one or more of the advantages that will be evident from the description. The present disclosure makes reference to one or more specific embodiments by way of illustration and example. It is understood, therefore, that the terminology, examples, drawings and embodiments are illustrative and are not intended to limit the scope of the disclosure.

Figure 1:
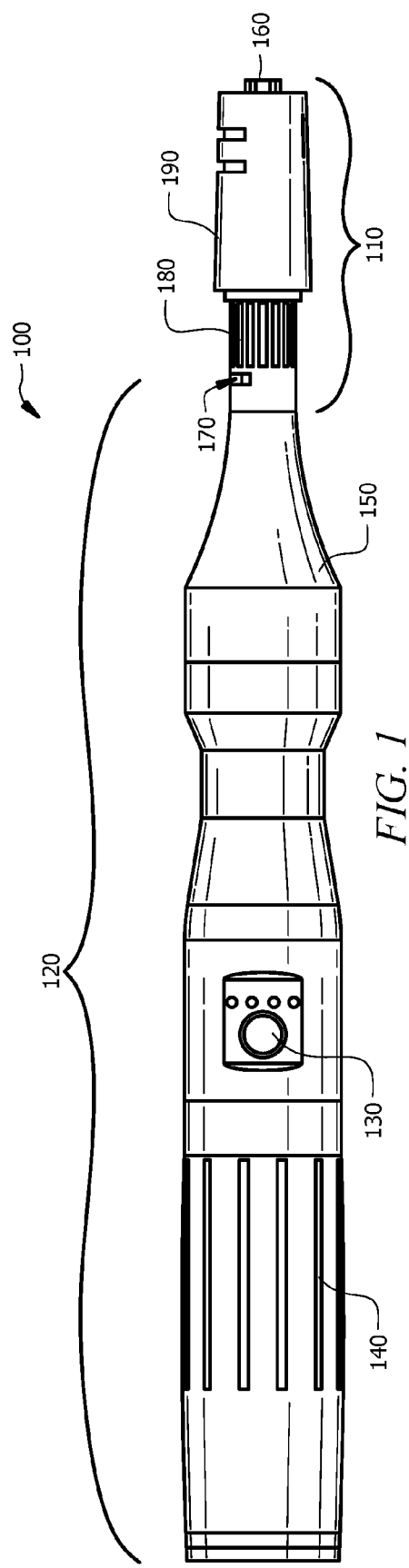
FIG. 1 illustrates an external side view of one embodiment of a microneedling apparatus that includes a disposable needle cartridge constructed in accordance with the disclosed principles.

FIG. 1 illustrates an external side view of one embodiment of a microneedling apparatus or device 100 (which may also be referred to as a "pen") that includes a disposable needle cartridge 110 constructed in accordance with the disclosed principles. The device 100 includes a main body 120 that houses the electric motor and associated circuitry, and externally includes one or more buttons 130 for ON/OFF operation of the device 100 as well as optional speed control depending on the model of device 100. The main body 120 also includes a handle area 140, which may include a textured surface for better gripping by a user during use of the device 100.

On the end of the main body 120 opposite the handle area 140, the device includes a front housing 150. The front housing 150 conceals the cam system that translates the spinning of the electric motor within the main body 120 into the reciprocating "in and out" motion used to drive the needle unit 160 housed within the needle cartridge 110. Accordingly, the front housing 150 may be removable from the remainder of the main body 120 in order to service the cam system, if needed. Additionally, the front housing 150 includes one or more attachment features 170 on its distal end which are configured to removably couple the needle cartridge 110 to the main body 120 of the device 100. Such attached feature(s) 170 may be any type of attachment configuration, such as the snap-fit type illustrated, or may even be threaded if desired.

The disposable needle cartridge 110 itself includes a base portion 180 on a proximal end, which is coupled to the main body 120, and the needle unit 160 on its distal end. The inner workings of the needle cartridge 110, which are not visible from this external view of the microneedling device 100, will be described in detail below. The needle cartridge 110 also includes a depth adjustment sleeve 190 movably coupled to a distal end of the base portion 180. In an advantageous embodiment, the depth adjustment sleeve 190 includes internal threads on the end proximal to the main body 120, while the distal end of the base portion 180 includes corresponding threads. With this type of threaded engagement between the depth adjustment sleeve 190 and the base portion 180 of the cartridge 110, the sleeve 190 may be rotated about the longitudinal axis of the device 100 to change its longitudinal distance with respect to the device 100. As the sleeve 190 moves closer to or farther from the main body 120, the needles of the needle unit 160 become more or less exposed, respectively, from within the sleeve 190. This allows a user to "dial in" the desired depth that the needles pierce the skin of a patient when the distal end of the sleeve 190 is pressed against the patient's skin during use of the device 100.

Moreover, the pitch of the threads connecting the sleeve 190 to the base portion 180 of the cartridge 110 may be selected fine enough such that very precise depth control of the needles is provided. Also, by providing needle depth control via the externally located sleeve 190, as opposed to conventional devices that provide needle depth control by actually adjusting the distance of the needle unit from the main body 120, not only is the disclosed depth adjustment system far less complex, but it is also far more precise since little to no play between the depth adjustment components exists. Thus, the disclosed depth adjustment system is not only more precise, but its more simplistic design greatly reduces manufacturing costs as compared to such conventional systems, as well as potential service or repair costs should such conventional systems fail.

Figure 2A:
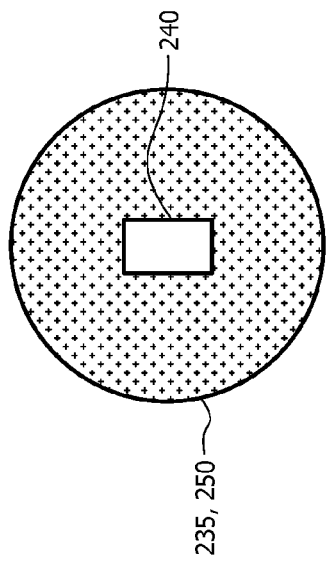
FIG. 2A illustrates a top view of an exemplary shape for the support members and absorbing members in the embodiment of the disposable needle cartridge illustrated in FIG. 2.
Figure 2:
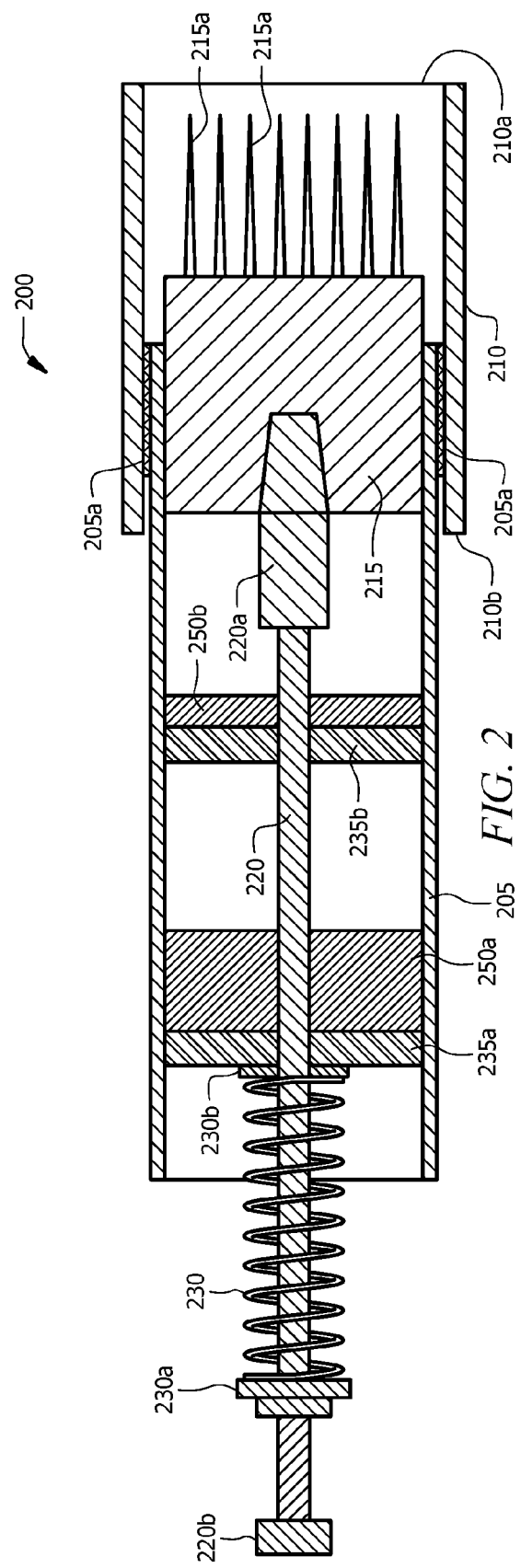
FIG. 2 illustrates a cross-sectional side view of one embodiment of a disposable needle cartridge constructed in accordance with the disclosed principles.

FIG. 2 illustrates a cross-sectional side view of one embodiment of a disposable needle cartridge 200 constructed in accordance with the disclosed principles. The needle cartridge 200 again includes a base portion 205, as well as a depth adjustment sleeve 210 and a needle unit 215.

In this embodiment, the depth adjustment sleeve 210 is rotationally coupled to the base portion 205 using threads 205a. As discussed above, the threaded attachment of the depth adjustment sleeve 210 to the base portion 205 allows a user to precisely adjust the maximum distance the needles 215a of the needle unit 215 will longitudinally extend beyond the distal end 210a of the depth adjustment sleeve 210. Moreover, a graduation scale (not illustrated) may be included on the external surface of the base portion 205 such that the proximal end 210b of the sleeve 210 aligns with graduations indicating to a user the specific maximum distance the needles 215a will extend beyond the distal end 210a of the sleeve 210 during use of the injection device to which the cartridge 200 is attached. Also as discussed above, the means by which the depth adjustment sleeve 210 is movably coupled to the base portion 205 may be different than the illustrated threaded attachment means, such as a sliding mechanism, while still falling within the broad scope of the present disclosure.

The needle cartridge 200 also includes a reciprocating drive shaft 220 passing through the base portion 205 and attaching to the needle unit 215. In the illustrated embodiment, the drive shaft 220 is connected to the needle unit 215 using a threaded end 220a, but any type of attachment means for connecting the drive shaft 220 to the needle unit 215 may also be employed within the broad scope of the disclosed principles. On a proximal end of the drive shaft 220 is a shaft cam member 220b configured to engage a corresponding drive motor cam member (not illustrated). As discussed above with the embodiment illustrated in FIG. 1, a drive motor within the main body of a microneedling device on which the disposable cartridge 200 includes a rotor shaft that rotates during operation of the injection device. The distal end of the rotor shaft is attached to the drive motor cam member such that it is rotated by the drive motor.

Within the cam mechanism, the rotation of the drive motor cam member is translated to the shaft cam member 220b such that the shaft cam member 220b is moved in and out longitudinally with respect the injection device. The cam mechanism can accomplish this simply by providing high and low surfaces within the drive motor cam member that contact the bottom surface of the shaft cam member 220b when it rotates. During this rotation, as the protruding high surfaces come into contact with the shaft cam member 220b, the drive shaft 220 is pushed away from the drive motor cam member. Conversely, once the high surface no longer are in contact with the shaft cam member 220b, a coil spring 230 is used to push the drive shaft 220 back towards the main body of the microneedling device such that the shaft cam member 220b now contacts the low, non-protruding surfaces of the drive motor cam member. Then, once again as the shaft cam member 220b encounters a high, protruding surface of the drive motor cam member, the shaft cam member 220b, and thus the drive shaft 220, is again push away from the main body of the microneedling device, which in turn compresses the coil spring 230 so that it may provide the force needed to push the drive shaft 220 back towards the device when needed.

Each time the cam mechanism causes the drive shaft 220 to move away and towards the main body of the microneedling device, the reciprocal drive shaft 220, which is affixed to the base of the needle unit 215, causes the needle unit 215 to correspondingly reciprocate away and towards the injection device within both the base portion 205 and the sleeve 210. It should be noted, of course, that any other type of mechanism used to translate the rotation of the drive motor's shaft to the reciprocating motion of the drive shaft 220 may also be employed with a disposable cartridge 200 according to the disclosed principles, and thus the discussed embodiment is merely exemplary. Consequently, when the distal end 210a of the sleeve 210 is held against the surface of the skin, this in and out movement of the needle unit 215 within the sleeve in turn causes the needles 215a to be extended beyond and be retracted within, respectively, the distal end 210a of the depth sleeve 210. This continuous extension beyond and retraction within the sleeve 210 is what provides the piercing or scratching of the skin by the needles 215a of the needle unit during use of the cartridge 200 during a microneedling procedure. In embodiments where the cartridge is used in a liquid injection microneedling procedure, injection of the liquid or other substance (e.g., from a fluid reservoir in the needle unit 215 and up through a plurality of liquid discharge holes at the base of the needles 215a) into a patient's skin.

The base portion 205 further includes therein one or more support members, which in this illustrated embodiment comprise two support members 235a, 235b. These support members 235a, 235b may be affixed to the interior of the base portion 205 to provide centering guides for the reciprocating drive shaft 220. Also, a first support member 235a may also provide a distal bearing surface 230b for a distal end of the coil spring 230, while a proximal bearing surface 230a for the coil spring 230 may be provide at an advantageous location on the drive shaft 220 itself. These bearing surfaces 230a, 230b allow the coil spring 230 to compress when the drive shaft 220 is moving outwardly, as well as provide the surfaces the compressed spring 230 pushes against to move the drive shaft 220 back inwardly during its reciprocating motion.

Moreover, these support members 235a, 235b may include a rectilinear aperture for the drive shaft 220 to pass through in embodiments where the drive shaft 220 has a corresponding rectilinear cross-section. Looking briefly at FIG. 2A, illustrated is a top view of an exemplary shape for the support members 235a, 235b. Specifically, to assist in preventing the drive shaft 220 from rotating as it reciprocates within the base portion 205, the cross-section of the drive shaft 220 may be non-circular in shape. The support members 235a, 235b may then each include an aperture 240 having a corresponding shape to the cross-section of the drive shaft 220, which would thus allow the drive shaft 220 to reciprocally (longitudinally) move through the support members 235a, 235b but prevent the drive shaft 220 from rotating as well. In the illustrated embodiment, the aperture 240 is shown as rectangular in shape, but any other non-circular shape, such as a square, triangle or any other non-circular shape, may instead be employed with the cross-section of the drive shaft 220 have a corresponding shape. Also, the attachment end 220a affixed to the needle unit 215, which may even be an extending base portion of the needle unit 215 itself that receives the end of the drive shaft 220 therein, may have the non-circular shape that passes through the aperture(s) while the drive shaft 220 maintains a typical round shape. In such embodiments, the non-circular attachment end or extending base portion of the needle unit would still assist in preventing rotation of the drive shaft as the drive shaft and needle unit reciprocate longitudinally. Such an embodiment is discussed with reference to FIGS. 3 and 3A below.

Returning to FIG. 2, the base portion 205 further includes one or more absorbing members that prevent patient blood and liquid mixture to be injected in the patient's skin from passing from the needle unit 215 through the base portion 205, and back into the main body of the microneedling device. Specifically, the absorbing members, which in this exemplary embodiment comprise two absorbing members 250a, 250b, are sized so that their external diameters contact the interior surface of the base portion 205, and their internal diameters contact the drive shaft 220. Moreover, in this embodiment, the absorbing members 250a, 250b each rest against one of the corresponding support members 235a, 235b. The absorbing members 250a, 250b are provided within a disposable needle cartridge 200 designed and constructed in accordance with the disclosed principles as a fluid barrier to prevent the backflow of blood discharged from the skin of a patient, as well as any injection liquid mixture, that may flow from the needle unit through the base portion 205 and back to the main body of the injection device during a medical procedure. Thus, the disclosed principles, rather than simply attempting to seal the cartridge from the main body of the microneedling device actually provides absorbing members to soak up and hold any such fluids that would otherwise backflow through the needle cartridge. Turning back briefly to FIG. 2A, the absorbing members 250a, 250b may also be formed with a non-circular shaped aperture 240 in those embodiments where the support members 235a, 235b also have a corresponding non-circular shape. Of course, if a drive shaft 220 with a circular cross-section is employed, both the support members 235a, 235b and absorbing members 250a, 250b may have corresponding circular apertures.

Moreover, multiple absorbing members may be employed in accordance with this technique, such as the illustrated use of two absorbing members 250a, 250b in FIG. 2. Furthermore, each such multiple absorbing member may be made in different sizes or thicknesses, also as provided in the exemplary embodiment of FIG. 2. The material used to form the absorbing members maybe any suitable material capable of absorbing these fluids, which could be an organic material such as cotton or even a synthetic material. Importantly, seals provided in needle cartridges typically need to be of a flexible nature for maximum effectiveness, and thus this limitation can create a "shelf life" for a needle cartridge only employing such seal material. More specifically, rubber or other similar material typically used for seals will dry out (i.e., "dry rot") over time, and thus it would be difficult for a user of such a needle cartridge to determine if the seal/seal material is still intact before use. In contrast, because the disclosed principles provide for an absorbing fluid barrier, as a needle cartridge with such a barrier sits over time, the absorbing members would not be at risk of drying out, and thus would maintain their ability to absorb indefinitely. As a result, a user could confidently use a needle cartridge as disclosed herein without risk that the fluid barrier has deteriorated.

Also, by providing a liquid or fluid barrier within a needle cartridge that absorbs substances rather than simply providing a seal against the backflow of such substances, the disclosed principles provide the further advantage that such backflowing liquids are also less likely to leak from the needle cartridge 200 once the cartridge is removed from the microneedling device. With conventional needle cartridges that simply provide seals, the backflowing liquids often still flow within the cartridge, and thus could leak from the needle unit end of the cartridge either while it is still attached to the microneedling device, or even after it has been removed. Such continued risk of flowing from a different area of the needle cartridge presents another unnecessary contamination risk beyond preventing backflow to the microneedling device. By providing a liquid barrier that is an absorption barrier rather than simply a seal, such continued risk of contamination is also eliminated. Moreover, the disclosed absorption barrier technique may even be combined with the use of one or more seals if desired.

Looking now at FIG. 3, illustrated is a cross-sectional side view of another embodiment of a disposable needle cartridge 300 constructed in accordance with the disclosed principles. This embodiment of the needle cartridge 300 again includes a base portion 305, as well as a depth adjustment sleeve 310 and a needle unit 315. In addition, this embodiment includes a drive shaft 320 passing through the base portion 305 and attached to the base of the needle unit 315 using an attachment member 320a also attached to the drive shaft. The opposing, proximal end of the drive shaft 320 (proximal again with respect to the microneedling device on which the cartridge 300 is mounted) again includes a cam member 320b for use in translating the rotation of a drive motor in the microneedling device (not illustrated) into longitudinal reciprocating motion of the drive shaft 320, as discussed in detail above.

This embodiment of the disposable needle cartridge 300 again includes a coil spring 330 for pushing the drive shaft 320 back towards the main body of a microneedling device to which the needle cartridge 300 is attached to assist with the reciprocating motion of the drive shaft 320. The coil spring 330 again sits between first and second bearing surfaces 330a, 330b that cause the coil spring 330 to compress when the drive shaft 320 is moving outwardly, as well as provide the surfaces the compressed spring 330 pushes against to move the drive shaft 320 back inwardly towards the microneedling device during its reciprocating motion. Also, this alternative embodiment includes a single absorbing member 350 that provides a liquid barrier in accordance with the disclosed principles. Accordingly, the absorbing member 350 may be comprised of an absorbing material such as cotton to prevent patient blood and/or liquid mixture being injected in the patient's skin from passing from the needle unit 315 through the base portion 305, and back into the main body of the microneedling device holding the needle cartridge 300. Thus, as before, the absorbing member 350 may be sized so that its external diameter contacts the interior surface of the base portion 305, and its internal diameter contacts the drive shaft 320. Moreover, the absorbing member 350 may be located so that it rests against one of the support members 335a, helping to keep it in position.

In addition, however, this embodiment of the disposable needle cartridge 300 now includes a seal member 360 attached to the outer surfaces of the bearing members 330a, 330b. More specifically, in this embodiment, a distal end of the seal member 360 is sealed to the second bearing member 330b, which in turn is sealed against (by being coupled to or simply formed with) the first support member 335a, which in turn is sealed against (again, by being coupled to or simply formed with) the inner surface of the base portion 305. Thus, at this end of the seal member 360, backflowing liquid(s) would likely only pass through the area(s) between the drive shaft 320 and the aperture of the first support member 335a, which is sealed by the distal end of the seal member 360. Also, a proximal end of the seal member 360 is sealed to the first bearing member 330a, which in turn is sealed against the drive shaft 320. Thus, at this end of the seal member 360, backflowing liquid(s) would likely only pass over the first bearing member 330a, which is sealed by the proximal end of the seal member 360. Accordingly, the seal member 360 is provided at the base of the needle cartridge 300 as a further fluid/liquid barrier, in addition to the absorbing barrier provided by absorbing member 350, to further help prevent the backflow of blood discharged from the skin of a patient, as well as any injection liquid mixture in liquid injection application, that may flow from the needle unit 315 through the base portion 305 and back to the main body of the microneedling device during a medical procedure.

The material comprising the seal member 360 may be any advantageous material that may provide an airtight or hermetic seal. For example, the seal member 360 may be made from one or more natural rubber material(s), such as latex, isoprene, polyisoprene and other natural elastomers, as well as one or more synthetic rubbers materials, such as styrene-butadiene rubbers (SBR) and other petroleum-derived synthetic elastomers. Of course, no limitation to the materials used for the seal member 360, or combinations thereof, is intended or should be implied. Accordingly, although not required, such a seal may be combined with the unique absorbing barrier of the disclosed principles to provide a combined protection structure against backflowing liquids from the needle unit 315 to the main body of the microneedling device on which the disposable needle cartridge 300 is mounted.

Also in this embodiment, the second support member 335b is configured to receive a portion of the attachment member 320a therethrough as the drive shaft 320 moves inwardly and outwardly during use. Additionally, as in the illustrated embodiment, the external shape of the attachment member 320a may be formed with a non-circular shape. Likewise, the corresponding aperture 340, which may be seen looking momentarily at FIG. 3A, of the second support member 335b may be of the same non-circular shape. Thus, as the aperture 340 of the second support member 335b receives the attachment member 320a therethrough during reciprocating movement of the drive shaft 320, the corresponding non-circular shapes of these components assist in preventing the drive shaft 320 from rotating about the longitudinal axis of the cartridge 300. Although the non-circular shape of the aperture 340, as well as the corresponding external shape of the portion of the attachment end 320b received therein, are illustrated as rectangular, it should be understood that any non-circular shape may be employed within the broad scope of the disclosed principles. Looking briefly at FIG. 3B, illustrated is a top view of an exemplary shape for the first support member and/or the absorbing member 350 in this embodiment of the disposable needle cartridge 300. As illustrated, the aperture 340a of the first support member 335a and/or the absorbing member 350 may be circular in shape in embodiments where the cross-sectional shape of the drive shaft 320 is also circular. As discussed above, however, other corresponding shapes between apertures of the first support member 335a/absorbing member 350 and the drive shaft 320 may also be employed.

Figure 4A:
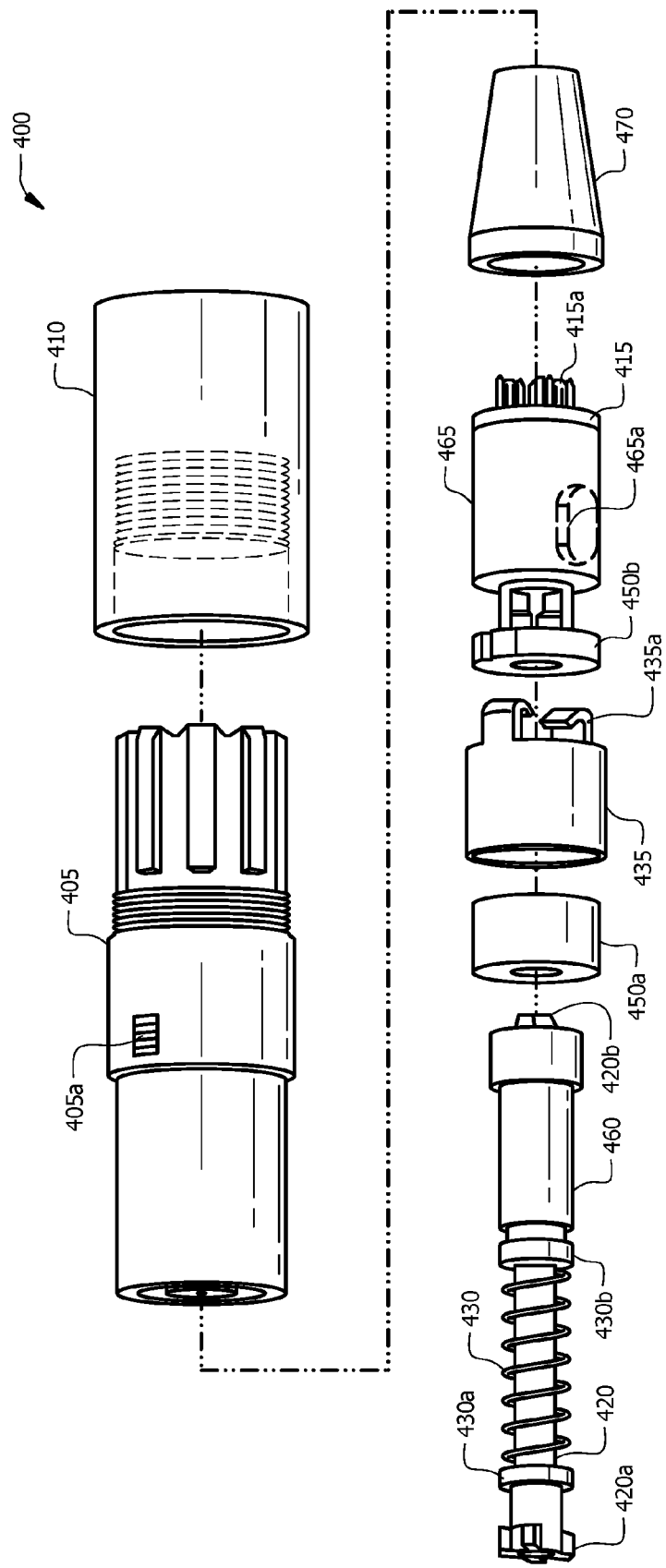
FIG. 4A illustrates an exploded side view of another embodiment of a disposable needle cartridge constructed in accordance with the disclosed principles.
Figure 4B:
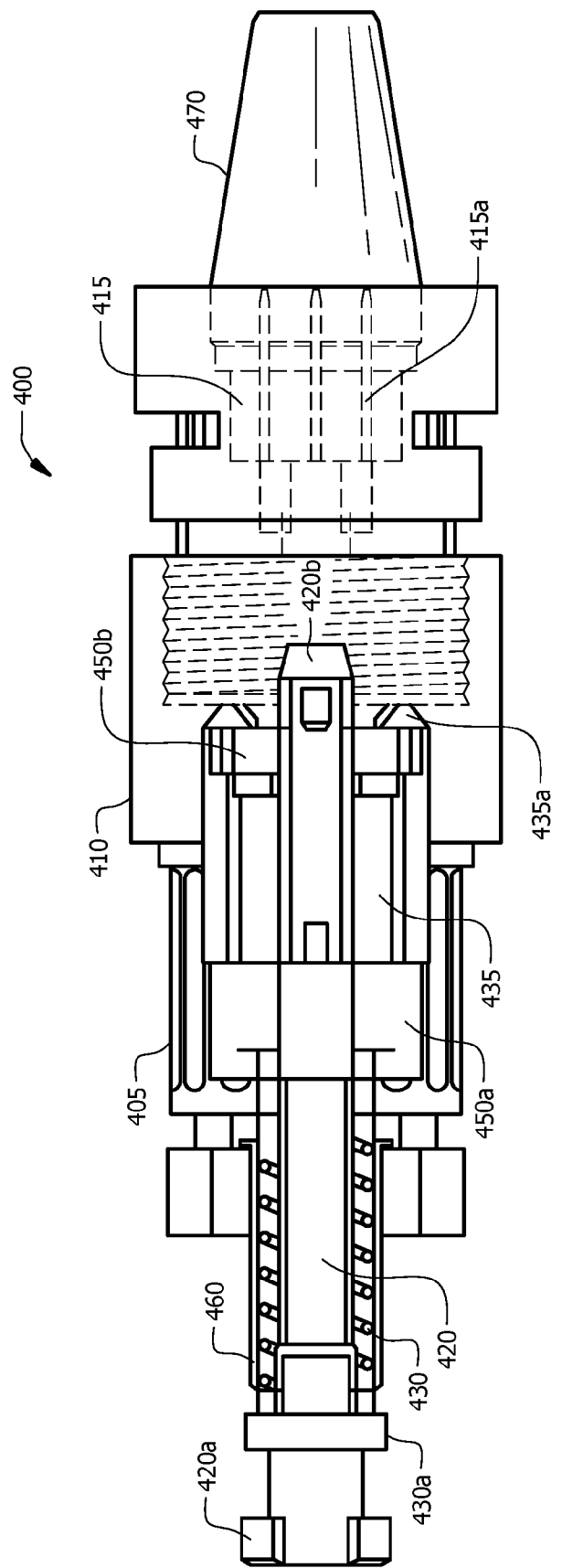
FIG. 4B illustrates a side view of the embodiment of the disposable needle cartridge shown in FIG. 4A in an assembled state.

Turning now to FIG. 4A, illustrated is an exploded side view of another embodiment of a disposable needle cartridge constructed in accordance with the disclosed principles. Additionally, FIG. 4B illustrates a side view of the embodiment of the disposable needle cartridge 400 shown in FIG. 4A in an assembled state. This third embodiment of a needle cartridge 400 according to the disclosed principles again includes a base portion 405, as well as a depth adjustment sleeve 410 and a needle unit 415. In addition, this embodiment includes a drive shaft that will attached to the base of the needle unit 415 using an attachment end 420a of the drive shaft 420. The opposing, proximal end of the drive shaft 420 again includes a cam member 420b for use in translating the rotation of a drive motor in the microneedling device, which in this embodiment of the cartridge 400 is a liquid injection device (not illustrated), into longitudinal reciprocating motion of the drive shaft 420, as discussed above. Of course, the illustrated embodiment of the cartridge 400 may be used with a non-liquid injection microneedling apparatus as well.

This embodiment of the disposable needle cartridge 400 also again includes a coil spring 430 for pushing the drive shaft 420 back towards the main body of a microneedling liquid injection device to which the needle cartridge 400 is attached to assist with the reciprocating motion of the drive shaft 420. The coil spring 430 again sits between first and second bearing surfaces 430a, 430b that cause the coil spring 430 to compress when the drive shaft 420 is moving outwardly, as well as provide the surfaces the compressed spring 430 pushes against to move the drive shaft 420 back inwardly towards the injection device during its reciprocating motion. However, in this embodiment, the second bearing surface 430b is located at the base of a seal member 460. This seal member 460 is provided as a sealing sleeve 460 that is positioned over the drive shaft 420. In such embodiments, the seal sleeve 460 may be formed from a rigid material, such as vulcanized rubber or even plastic. Moreover, the seal sleeve 460 may be formed partially of rigid materials, such as at the second bearing surface 430b to provide sufficient resiliency against the coil spring 330, and partially non-rigid materials that may provide better sealing properties against the drive shaft 420, such as any of the seal materials disclosed above with reference to FIG. 3.

Also, this embodiment includes a first and second absorbing members 450a, 450b that provides a further liquid barrier, and more accurately an absorbing barrier, as compared to the seal sleeve 460. Thus, as before, the absorbing members 450a, 450b may be comprised of an absorbing material such as cotton to prevent patient blood and liquid mixture being injected in the patient's skin from passing from the needle unit 415 through the base portion 405, and back into the main body of the microneedling device holding the needle cartridge 400. Also as before, the absorbing members 450a, 450b may be sized so that their external diameters contact the interior surface of the base portion 405, and their internal diameters contact the drive shaft 420. In such embodiments, the drive shaft 420 may have a circular cross-section, as illustrated, while the absorbing members 450a, 450b have corresponding circular shaped apertures therethrough. Alternatively, the drive shaft 420 or an attachment portion for the drive shaft 420 to the needle unit 415 may have a non-circular shape, with the absorbing members 450a, 450b having corresponding non-circular apertures, as discussed above. For this illustrated embodiment, the first absorbing member 450a is positioned between the distal end of the seal sleeve 460 and a single support member 435 size to contact the interior diameter of the base portion 405. Moreover, the support member 435 in this embodiment includes grasping features 435a use to hold the second absorbing member 450b in a desired position.

A liquid reservoir 465, which receives the needle unit 415 therein, may then rest directly on, or simply proximal to, the second absorbing member 450b. The reservoir 465 is used to hold the liquid(s) being injected into a patients skin during use of a liquid injection microneedling device holding the cartridge 400, and which may be dispensed into the reservoir 465 through a liquid dispensing aperture 465a. During use on a patient's skin, such as fro tattooing or collagen injections, the liquid(s) pass through the needle unit 415 and onto the needles 415a extending beyond the depth adjusting sleeve 410. The threads used to position the depth sleeve 410 with respect to the base portion 405 may be seen in FIG. 4A, as well as the graduation scale 405a placed on the exterior surface of the base portion 405 that provides the user the precise maximum distance the needles 415a will extend beyond the depth adjustment sleeve 410 during use of the microneedling device. Finally, in this embodiment of a disposable needle cartridge 400 of the present invention, a protective cap 470 may also be provide to not only cover the needles 415a but also to provide a seal for liquids that may be present in the reservoir 465.

Referring now to FIG. 5, illustrated is a cross-sectional side view of yet another embodiment of a disposable needle cartridge 500 constructed in accordance with the disclosed principles. This embodiment of the needle cartridge 500 again includes a base portion 505, as well as a depth adjustment sleeve 510 and a needle unit 515. However, in this embodiment, the base portion is comprised of first base portion 505a and a second base portion 505b. As illustrated, the two base portions 505a, 505b may be manufactured with two different outer diameters. However, the two base portions 505a, 505b may still be manufactured as a single, integral piece, if desired.

As in other embodiments, this embodiment again includes a drive shaft 520 passing through the two base portions 505a, 505b and attached to the base of the needle unit 515 using an attachment member 520a also attached to the drive shaft. The opposing, proximal end of the drive shaft 520 (proximal again with respect to the microneedling device on which the cartridge 500 is mounted) again includes a cam member 520b for use in translating the rotation of a drive motor in the microneedling device (not illustrated) into longitudinal reciprocating motion of the drive shaft 520, as discussed in detail above.

This embodiment of the disposable needle cartridge 500 again includes a coil spring 530 for pushing the drive shaft 520 back towards the main body of a microneedling device to which the needle cartridge 500 is attached to assist with the reciprocating motion of the drive shaft 520. The coil spring 530 again sits between first and second bearing surfaces 530a, 530b that cause the coil spring 530 to compress when the drive shaft 520 is moving outwardly, as well as provide the surfaces the compressed spring 530 pushes against to move the drive shaft 520 back inwardly towards the microneedling device during its reciprocating motion. Also, this alternative embodiment includes a single absorbing member 550 that provides a liquid barrier in accordance with the disclosed principles. Accordingly, the absorbing member 550 may be comprised of an absorbing material such as cotton to prevent patient blood and/or any liquid mixture being injected in the patient's skin from passing from the needle unit 515 through the base portion 505, and back into the main body of the microneedling device holding the needle cartridge 500. Thus, as before, the absorbing member 550 may be sized so that its external diameter contacts the interior surface of the base first portion 505a, and its internal diameter contacts the drive shaft 520. Moreover, the absorbing member 550 may be located so that it rests against one of the support members 535a, helping to keep it in position.

In addition, this embodiment of the disposable needle cartridge 500 also includes a seal member 560 attached to the outer surfaces of the bearing members 530a, 530b. As before, a distal end of the seal member 560 is sealed to the second bearing member 530b, which in turn is sealed against (by being coupled to or simply formed with) the first support member 535a, which in turn is sealed against (again, by being coupled to or simply formed with) the inner surface of the first base portion 505a. Thus, at this end of the seal member 560, backflowing liquid(s) would likely only pass through the area(s) between the drive shaft 520 and the aperture of the first support member 535a, which is sealed by the distal end of the seal member 560. Also, a proximal end of the seal member 560 is sealed to the first bearing member 530a, which in turn is sealed against the drive shaft 520. Thus, at this end of the seal member 560, backflowing liquid(s) would likely only pass over the first bearing member 530a, which is sealed by the proximal end of the seal member 560. Accordingly, the seal member 560 is provided at the base of the needle cartridge 500 as a further fluid/liquid barrier, in addition to the absorbing barrier provided by absorbing member 550, to further help prevent the backflow of blood discharged from the skin of a patient, as well as any injection liquid mixture, that may flow from the needle unit 515 through the base portion 505 and back to the main body of the microneedling device during a microneedling transdermal procedure.

The material comprising the seal member 560 may be any advantageous material that may provide an airtight or hermetic seal. For example, the seal member 560 may be made from one or more natural rubber material(s), such as latex, isoprene, polyisoprene and other natural elastomers, as well as one or more synthetic rubbers materials, such as styrene-butadiene rubbers (SBR) and other petroleum-derived synthetic elastomers. Of course, no limitation to the materials used for the seal member 560, or combinations thereof, is intended or should be implied. Accordingly, although not required, such a seal may be combined with the unique absorbing barrier of the disclosed principles to provide a combined protection structure against backflowing liquids from the needle unit 515 to the main body of the microneedling device on which the disposable needle cartridge 500 is mounted.

Also in this embodiment, the second support member 535b is configured to receive a portion of the attachment member 520a therethrough as the drive shaft 520 moves inwardly and outwardly during use. Additionally, as in the illustrated embodiment, the external shape of the attachment member 520a may again be formed with a non-circular shape. Likewise, the corresponding aperture 540, which may be seen looking briefly at FIG. 5A, of the second support member 535b may be of the same non-circular shape. Thus, as the aperture 540 of the second support member 535b receives the attachment member 520a therethrough during reciprocating movement of the drive shaft 520, the corresponding non-circular shapes of these components assist in preventing the drive shaft 520 from rotating about the longitudinal axis of the cartridge 500. Although the non-circular shape of the aperture 540, as well as the corresponding external shape of the portion of the attachment end 520b received therein, are illustrated as rectangular, it should be understood that any non-circular shape may be employed within the broad scope of the disclosed principles. Moreover, turning briefly to FIG. 5B, the first support member 535a and the absorbing member 550 may have circular apertures 540a therethrough, which would correspond to the cross-sectional shape of the drive shaft 520. In other embodiments, these components could additionally, or alternatively, have the non-circular cross-sectional/aperture shapes to assist in prevent rotation of the needle unit 515 during use of the cartridge 500. In yet other embodiments, all of the applicable components simply have corresponding circular shapes.

The embodiment of the needling cartridge 500 illustrated in FIG. 5 also differs from prior embodiments in that the depth adjustment sleeve 510 is configured to be received within the second base portion 505b, rather than over its exterior surface. As such, threads 505c are formed on the exterior surface of the proximal end of the depth adjustment sleeve 510, as well as on the interior surface of the distal end of the second base portion 505b. As with other embodiments, the threaded attachment of the depth adjustment sleeve 510 to the base portion 505b allows a user to precisely adjust the maximum distance the needles 515a of the needle unit 515 will longitudinally extend beyond the distal end 510a of the depth adjustment sleeve 510. A graduation scale (not illustrated) may thus be included on the external surface of the depth adjustment sleeve 510 such that the distal end of the second base portion 505b aligns with graduations on the exterior of the depth adjusting sleeve 510 indicating to a user the specific maximum distance the needles 515a will extend beyond the distal end 510a of the sleeve 510 during use of the injection device to which the cartridge 500 is attached. Also as before, the means by which the depth adjustment sleeve 510 is movably coupled to the base portion 505b may be different than the illustrated threaded attachment means, while still falling within the broad scope of the present disclosure.

Figure 6C:
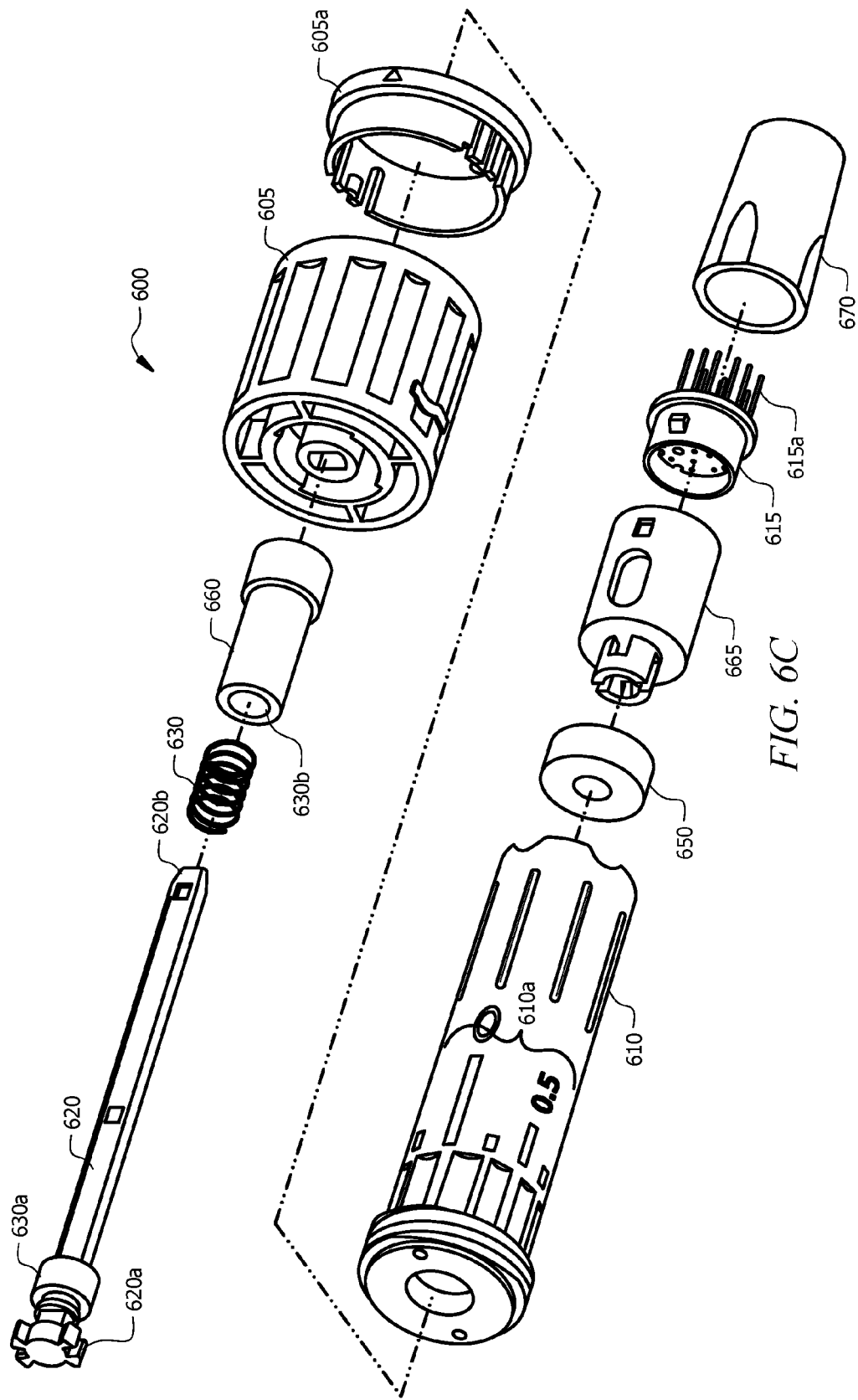
FIG. 6C illustrates an exploded view of the embodiment of a disposable needle cartridge illustrated in FIGS. 6A and 6B.

Looking now collectively at FIG. 6A and FIG. 6B, illustrated are normal and cross-sectional side views, respectively, of yet another embodiment of a disposable needle cartridge 600 constructed in accordance with the disclosed principles. This embodiment of the needle cartridge 600 again includes a base portion 610, as well as a depth adjustment sleeve 605 and a needle unit 615. One end of the base portion 610 is moveably connected within the adjustment sleeve 605, for example, via a threaded connection. Also in this embodiment, the adjustment sleeve 605 cooperates with a retainer ring 605a to keep the base portion 610 in position, as well as to prevent the base portion 610 from extending too far. FIG. 6C illustrates an exploded view of this embodiment of the disposable needle cartridge 600. In this exploded view, the details of each of the individual components comprising the needle cartridge 600 may be seen, as well as one of the way they may be assembled into the finished cartridge 600.

As in other embodiments, this embodiment again includes a drive shaft 620 passing through the base portion 610 and adjustment sleeve 605, and attached to the base of the needle unit 615 using an attachment member attached to the attachment end of the drive shaft 620. The opposing, proximal end of the drive shaft 620 (proximal once again with respect to the microneedling device on which the cartridge 600 is mounted) again includes a cam member 620b for use in translating the rotation of a drive motor in the microneedling device (not illustrated) into longitudinal reciprocating motion of the drive shaft 620, as discussed in detail above.

This embodiment of the disposable needle cartridge 600 also again includes a coil spring 630 for pushing the drive shaft 620 back towards the main body of a microneedling device to which the needle cartridge 600 is attached to assist with the reciprocating motion of the drive shaft 620. The coil spring 630 again sits between first and second bearing surfaces 630a, 630b that cause the coil spring 630 to compress when the drive shaft 620 is moving outwardly, as well as provide the surfaces the compressed spring 630 pushes against to move the drive shaft 620 back inwardly towards the microneedling device during its reciprocating motion. Also, this embodiment includes a single absorbing member 650 that provides a liquid barrier in accordance with the disclosed principles. Accordingly, the absorbing member 650 may be comprised of an absorbing material such as cotton to prevent patient blood and/or any liquid mixture being injected in the patient's skin from passing from the needle unit 615 through the base portion 610, and back into the main body of the microneedling device holding the needle cartridge 600. Thus, as before, the absorbing member 650 may be sized so that its external diameter contacts the interior surface of the base portion 610, and its internal diameter contacts the drive shaft 620.

A liquid reservoir 665, which receives the needle unit 615 therein, may again be employed in some embodiments. As discussed above, such a reservoir 665 is used to hold the liquid(s) being injected into a patients skin during use of a liquid injection microneedling device holding the cartridge 600, and which may be dispensed into the reservoir 665 through a liquid dispensing aperture. Also in this embodiment as with others, a protective cap 670 may be provide to not only cover the needles 615a, but also to provide a seal for liquids that may be present in the reservoir 665.

In addition, this embodiment of the disposable needle cartridge 600 also includes a seal member 660 attached to the outer surfaces of the bearing members 630a, 630b. As before, a distal end of the seal member 660 is sealed to the second bearing member 630b, which in turn is sealed against (by being coupled to or simply formed with) a support member of the adjustment sleeve. Thus, at this end of the seal member 660, backflowing liquid(s) would likely only pass through the area(s) between the drive shaft 620 and the aperture of the support member, which is sealed by the distal end of the seal member 660. That this support member is part of the internal construction of the adjustment sleeve 605, rather than the base portion 610, is another unique feature of this embodiment. Also, a proximal end of the seal member 660 is sealed to the first bearing member 630a, which in turn is sealed against the drive shaft 620. Thus, at this end of the seal member 660, backflowing liquid(s) would likely only pass over the first bearing member 630a, which is sealed by the proximal end of the seal member 660. Accordingly, the seal member 660 is provided at the base of the needle cartridge 600 as a further fluid/liquid barrier, in addition to the absorbing barrier provided by absorbing member 650, to further help prevent the backflow of blood discharged from the skin of a patient, as well as any injection liquid mixture, that may flow from the needle unit 615 through the base portion 610 and back to the main body of the microneedling device during a microneedling transdermal procedure.

The material comprising the seal member 660 may again be any advantageous material that may provide an airtight or hermetic seal. For example, the seal member 660 may be made from one or more natural rubber material(s), such as latex, isoprene, polyisoprene and other natural elastomers, as well as one or more synthetic rubbers materials, such as styrene-butadiene rubbers (SBR) and other petroleum-derived synthetic elastomers. Of course, no limitation to the materials used for the seal member 660, or combinations thereof, is intended or should be implied. Accordingly, although not required, such a seal may be combined with the unique absorbing barrier of the disclosed principles to provide a combined protection structure against backflowing liquids from the needle unit 615 to the main body of the microneedling device on which the disposable needle cartridge 600 is mounted.

This embodiment of the needling cartridge 600 also differs from prior embodiments in that the depth adjustment sleeve 605 is configured to receive the proximal end of the base portion 610. As such, threads are formed on the exterior surface of the proximal end of the base portion 610, as well as on the interior surface of the distal end of the adjustment sleeve 605. As with other embodiments, the threaded attachment of the base portion 610 to the adjustment sleeve 605 allows a user to precisely adjust the maximum distance the needles 615a of the needle unit 615 will longitudinally extend beyond the distal end of the base portion 610. A graduation scale 610a may thus be included on the external surface of the base portion 610 such that the distal end of the adjustment sleeve 605 (where the retainer ring 605a is located) aligns with graduations on the exterior of the base portion 610 indicating to a user the specific maximum distance the needles 615a will extend beyond the distal end of the base portion 610 during use of the injection device to which the cartridge 600 is attached. Also as before, the means by which the depth adjustment sleeve 605 is movably coupled to the base portion 610 may be different than the illustrated threaded attachment means, while still falling within the broad scope of the present disclosure.

In the numerous embodiments of the inventive subject matter disclosed herein, such embodiments may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the claims reflect, inventive subject matter lies in less than all features of a single disclosed embodiment. Thus the following claims are hereby incorporated into the Detailed Description, with each claim standing on its own as a separate embodiment.

The description has made reference to several exemplary embodiments. It is understood, however, that the words that have been used are for description and illustration, rather than words of limitation. Changes may be made within the purview of the appended claims, as presently stated and as amended, without departing from the scope and spirit of the disclosure in all its aspects. Although this description makes reference to particular means, materials and embodiments, the disclosure is not intended to be limited to the particulars disclosed; rather, the disclosure extends to all functionally equivalent technologies, structures, methods and uses such as are within the scope of the appended claims.

What is claimed is:

1. A needle cartridge for use with a transdermal microneedling apparatus, the needle cartridge comprising:
   a base portion having a proximal end proximate to the apparatus, and having a distal end opposite its proximal end;
   a sleeve having a proximal end coupled to the distal end of the base portion, and having a distal end opposite its proximal end;
   a needle unit disposed at the distal end of the base portion and within the sleeve, the needle unit comprising at least one needle extending therefrom towards the distal end of the sleeve;
   a drive shaft disposed through the base portion and coupled to the needle unit, the drive shaft configured to be driven reciprocally along a longitudinal axis of the base portion by a drive system of the apparatus, and thereby move the needle unit reciprocally along the longitudinal axis of the base portion such that the at least one needle of the needle unit extends beyond and retracts within the distal end of the sleeve; and
   an absorbing barrier disposed within the base portion and configured to prevent the backflow of liquid from the needle unit through the base portion during use of the apparatus, wherein the absorbing barrier comprises at least one absorbing member having an outer dimension in contact with an interior surface of the base portion.

2. A needle cartridge in accordance with claim 1, wherein the sleeve is a depth adjustment sleeve movable with respect to the base portion in order to adjust a maximum distance the at least one needle extends beyond the distal end of the sleeve.

3. A needle cartridge in accordance with claim 2, wherein the depth adjustment sleeve is rotationally coupled to the base portion using threads.

4. A needle cartridge in accordance with claim 2, wherein the base portion further comprises graduations disposed thereon such that the proximal end of the sleeve aligns with the graduations to indicate a maximum distance the at least one needle will extend beyond the distal end of the sleeve.

5. A needle cartridge in accordance with claim 1, wherein the at least one absorbing member further comprises an inner dimension in contact with the drive shaft.

6. A needle cartridge in accordance with claim 1, wherein the at least one absorbing member further comprises a surface in contact with a base of the needle unit.

7. A needle cartridge in accordance with claim 1, wherein the at least one absorbing member comprises an organic absorbing material or a synthetic absorbing material.

8. A needle cartridge in accordance with claim 1, further comprising a fluid reservoir coupled to a base of the needle unit and configured to hold a liquid for dispensing via the needle unit, wherein the at least one absorbing member further comprises a surface in contact with a base of the fluid reservoir.

9. A needle cartridge in accordance with claim 1, further comprising a spring configured to compress when the drive shaft longitudinally moves in a first direction from the proximal end of the base portion to the distal end of the base portion, and to expand to move the drive shaft back in a second direction opposite to the first direction.

10. A needle cartridge in accordance with claim 9, further comprising a seal disposed over at least a portion of the drive shaft proximate to the spring.

11. A needle cartridge in accordance with claim 1, further comprising at least one support member attached to an inner diameter of the base portion and configured to guide the drive shaft during its reciprocal movement, wherein the at least one support member comprises a non-circular aperture therethrough configured to prevent rotation of the drive shaft during its reciprocal movement.

12. A needle cartridge in accordance with claim 11, wherein the drive shaft comprises a non-circular cross-section corresponding to the non-circular aperture to prevent rotation of the drive shaft during its reciprocal movement.

13. A needle cartridge in accordance with claim 11, further comprising an attachment member for use in coupling a distal end of the drive shaft to a base of the needle unit, the attachment member comprising a non-circular cross-section corresponding to the non-circular aperture to prevent rotation of the drive shaft during its reciprocal movement.

14. A needle cartridge for use with a transdermal microneedling apparatus, the needle cartridge comprising:

a base portion having a proximal end proximate to the apparatus, and having a distal end opposite its proximal end;

a sleeve having a proximal end coupled to the distal end of the base portion, and having a distal end opposite its proximal end, wherein the sleeve is a depth adjustment sleeve movable with respect to the base portion in order to adjust a maximum distance the at least one needle extends beyond the distal end of the sleeve, and wherein the depth adjustment sleeve is rotationally coupled to the base portion using threads;

a needle unit disposed at the distal end of the base portion and within the sleeve, the needle unit comprising at least one needle extending therefrom towards the distal end of the sleeve;

a drive shaft disposed through the base portion and coupled to the needle unit, the drive shaft configured to be driven reciprocally along a longitudinal axis of the base portion by a drive system of the apparatus, and thereby move the needle unit reciprocally along the longitudinal axis of the base portion such that the at least one needle of the needle unit extends beyond and retracts within the distal end of the sleeve; and an absorbing barrier disposed within the base portion and configured to prevent the backflow of liquid from the needle unit through the base portion during use of the apparatus.

15. A needle cartridge in accordance with claim 14, wherein the base portion further comprises graduations disposed thereon such that the proximal end of the sleeve aligns with the graduations to indicate a maximum distance the at least one needle will extend beyond the distal end of the sleeve.

16. A needle cartridge in accordance with claim 14, wherein the absorbing barrier comprises at least one absorbing member having an outer dimension in contact with an interior surface of the base portion.

17. A needle cartridge in accordance with claim 16, wherein the at least one absorbing member further comprises an inner dimension in contact with the drive shaft.

18. A needle cartridge in accordance with claim 16, wherein the at least one absorbing member further comprises a surface in contact with a base of the needle unit.

19. A needle cartridge in accordance with claim 16, wherein the at least one absorbing member comprises an organic absorbing material or a synthetic absorbing material.

20. A needle cartridge in accordance with claim 16, further comprising a fluid reservoir coupled to a base of the needle unit and configured to hold a liquid for dispensing via the needle unit, wherein the at least one absorbing member further comprises a surface in contact with a base of the fluid reservoir.

21. A needle cartridge in accordance with claim 14, further comprising a spring configured to compress when the drive shaft longitudinally moves in a first direction from the proximal end of the base portion to the distal end of the base portion, and to expand to move the drive shaft back in a second direction opposite to the first direction.

22. A needle cartridge in accordance with claim 21, further comprising a seal disposed over at least a portion of the drive shaft proximate to the spring.

23. A needle cartridge in accordance with claim 14, further comprising at least one support member attached to an inner diameter of the base portion and configured to guide the drive shaft during its reciprocal movement, wherein the at least one support member comprises a non-circular aperture therethrough configured to prevent rotation of the drive shaft during its reciprocal movement.

24. A needle cartridge in accordance with claim 23, wherein the drive shaft comprises a non-circular cross-section corresponding to the non-circular aperture to prevent rotation of the drive shaft during its reciprocal movement.

25. A needle cartridge in accordance with claim 14, further comprising an attachment member for use in coupling a distal end of the drive shaft to a base of the needle unit, the attachment member comprising a non-circular cross-section corresponding to the non-circular aperture to prevent rotation of the drive shaft during its reciprocal movement.

26. A needle cartridge for use with a transdermal microneedling apparatus, the needle cartridge comprising:

a base portion having a proximal end proximate to the apparatus, and having a distal end opposite its proximal end;

a sleeve having a proximal end coupled to the distal end of the base portion, and having a distal end opposite its proximal end;

a needle unit disposed at the distal end of the base portion and within the sleeve, the needle unit comprising at least one needle extending therefrom towards the distal end of the sleeve;

a drive shaft disposed through the base portion and coupled to the needle unit, the drive shaft configured to be driven reciprocally along a longitudinal axis of the base portion by a drive system of the apparatus, and thereby move the needle unit reciprocally along the longitudinal axis of the base portion such that the at least one needle of the needle unit extends beyond and retracts within the distal end of the sleeve;

an absorbing barrier disposed within the base portion and configured to prevent the backflow of liquid from the needle unit through the base portion during use of the apparatus; and a spring configured to compress when the drive shaft longitudinally moves in a first direction from the proximal end of the base portion to the distal end of the base portion, and to expand to move the drive shaft back in a second direction opposite to the first direction.

27. A needle cartridge in accordance with claim 26, wherein the sleeve is a depth adjustment sleeve movable with respect to the base portion in order to adjust a maximum distance the at least one needle extends beyond the distal end of the sleeve.

28. A needle cartridge in accordance with claim 27, wherein the depth adjustment sleeve is rotationally coupled to the base portion using threads.

29. A needle cartridge in accordance with claim 27, wherein the base portion further comprises graduations disposed thereon such that the proximal end of the sleeve aligns with the graduations to indicate a maximum distance the needles will extend beyond the distal end of the sleeve.

30. A needle cartridge in accordance with claim 26, wherein the absorbing barrier comprises at least one absorbing member having an outer dimension in contact with an interior surface of the base portion.

31. A needle cartridge in accordance with claim 30, wherein the at least one absorbing member further comprises an inner dimension in contact with the drive shaft.

32. A needle cartridge in accordance with claim 30, wherein the at least one absorbing member further comprises a surface in contact with a base of the needle unit.

33. A needle cartridge in accordance with claim 30, wherein the at least one absorbing member comprises an organic absorbing material or a synthetic absorbing material.

34. A needle cartridge in accordance with claim 30, further comprising a fluid reservoir coupled to a base of the needle unit and configured to hold a liquid for dispensing via the needle unit, wherein the at least one absorbing member further comprises a surface in contact with a base of the fluid reservoir.

35. A needle cartridge in accordance with claim 26, further comprising a seal disposed over at least a portion of the drive shaft proximate to the spring.

36. A needle cartridge in accordance with claim 26, further comprising at least one support member attached to an inner diameter of the base portion and configured to guide the drive shaft during its reciprocal movement, wherein the at least one support member comprises a non-circular aperture therethrough configured to prevent rotation of the drive shaft during its reciprocal movement.

37. A needle cartridge in accordance with claim 36, wherein the drive shaft comprises a non-circular cross-section corresponding to the non-circular aperture to prevent rotation of the drive shaft during its reciprocal movement.

38. A needle cartridge in accordance with claim 36, further comprising an attachment member for use in coupling a distal end of the drive shaft to a base of the needle unit, the attachment member comprising a non-circular cross-section corresponding to the non-circular aperture to prevent rotation of the drive shaft during its reciprocal movement.

39. A needle cartridge for use with a transdermal microneedling apparatus, the needle cartridge comprising:
a base portion having a proximal end proximate to the apparatus, and having a distal end opposite its proximal end;
a sleeve having a proximal end coupled to the distal end of the base portion, and having a distal end opposite its proximal end;
a needle unit disposed at the distal end of the base portion and within the sleeve, the needle unit comprising at least one needle extending therefrom towards the distal end of the sleeve;
a drive shaft disposed through the base portion and coupled to the needle unit, the drive shaft configured to be driven reciprocally along a longitudinal axis of the base portion by a drive system of the apparatus, and thereby move the needle unit reciprocally along the longitudinal axis of the base portion such that the at least one needle of the needle unit extends beyond and retracts within the distal end of the sleeve;
an absorbing barrier disposed within the base portion and configured to prevent the backflow of liquid from the needle unit through the base portion during use of the apparatus; and
at least one support member attached to an inner diameter of the base portion and configured to guide the drive shaft during its reciprocal movement, wherein the at least one support member comprises a non-circular aperture therethrough configured to prevent rotation of the drive shaft during its reciprocal movement.

40. A needle cartridge in accordance with claim 39, wherein the sleeve is a depth adjustment sleeve movable with respect to the base portion in order to adjust a maximum distance the needles extend beyond the distal end of the sleeve.

41. A needle cartridge in accordance with claim 40, wherein the depth adjustment sleeve is rotationally coupled to the base portion using threads.

42. A needle cartridge in accordance with claim 40, wherein the base portion further comprises graduations disposed thereon such that the proximal end of the sleeve aligns with the graduations to indicate a maximum distance the needles will extend beyond the distal end of the sleeve.

43. A needle cartridge in accordance with claim 39, wherein the absorbing barrier comprises at least one absorbing member having an outer dimension in contact with an interior surface of the base portion.

44. A needle cartridge in accordance with claim 43, wherein the at least one absorbing member further comprises an inner dimension in contact with the drive shaft.

45. A needle cartridge in accordance with claim 43, wherein the at least one absorbing member further comprises a surface in contact with a base of the needle unit.

46. A needle cartridge in accordance with claim 43, wherein the at least one absorbing member comprises an organic absorbing material or a synthetic absorbing material.

47. A needle cartridge in accordance with claim 43, further comprising a fluid reservoir coupled to a base of the needle unit and configured to hold a liquid for dispensing via the needle unit, wherein the at least one absorbing member further comprises a surface in contact with a base of the fluid reservoir.

48. A needle cartridge in accordance with claim 39, further comprising a spring configured to compress when the drive shaft longitudinally moves in a first direction from the proximal end of the base portion to the distal end of the base portion, and to expand to move the drive shaft back in a second direction opposite to the first direction.

49. A needle cartridge in accordance with claim 48, further comprising a seal disposed over at least a portion of the drive shaft proximate to the spring.

50. A needle cartridge in accordance with claim 39, wherein the drive shaft comprises a non-circular cross-section corresponding to the non-circular aperture to prevent rotation of the drive shaft during its reciprocal movement.

51. A needle cartridge in accordance with claim 39, further comprising an attachment member for use in coupling a distal end of the drive shaft to a base of the needle unit, the attachment member comprising a non-circular cross-section corresponding to the non-circular aperture to prevent rotation of the drive shaft during its reciprocal movement.

* * * * *